US00PP33143P2

(12) United States Plant Patent
Swartout et al.

(10) Patent No.: US PP33,143 P2
(45) Date of Patent: Jun. 8, 2021

(54) ***CANNABIS RUDERALIS + HUMULUS LUPULUS* PLANT NAMED 'ANEW'**

(50) Latin Name: *Cannabis ruderalis + Humulus lupulus*
Varietal Denomination: ANEW

(71) Applicant: Anewsha Holding Group LLC, San Juan, PR (US)

(72) Inventors: Christopher Swartout, Brooklyn, NY (US); Peter Horst Behncke, Jackson, MI (US)

(73) Assignee: Anewsha Holding Group LLC, San Juan, PR (US)

( * ) Notice: Subject to any disclaimer, the term of this patent is extended or adjusted under 35 U.S.C. 154(b) by 0 days.

(21) Appl. No.: 16/501,096

(22) Filed: Feb. 22, 2019

(51) Int. Cl.
*A01H 5/02* (2018.01)
*A01H 6/28* (2018.01)

(52) U.S. Cl.
USPC ..... Plt./258

(58) Field of Classification Search
USPC ..... Plt./258, 263.1, 236
CPC ... A01H 5/08; A01H 5/12; A01H 5/02; A01H 5/00; A01H 6/28
See application file for complete search history.

(56) References Cited

PUBLICATIONS

Scripta Horticulturae No. 10 International Code of Nomenclature for Cultivated Plants Eighth Edition 2009, two cover pages,pp. 37-38 (Year: 2009).*

* cited by examiner

*Primary Examiner* — June Hwu
(74) *Attorney, Agent, or Firm* — McDonnell Boehnen Hulbert & Berghoff LLP

(57) ABSTRACT

This present disclosure relates to a new and distinct *Cannabis ruderalis + Humulus lupulus* plant named 'ANEW' particularly characterized by flowers that autoflower ripen every 45-90 days and which are green or mottled with silver grey. Plant which may be propagated economically and uniformly using tissue culture, root grafting and produce a high yield 100% phytocannabinoid molecule "CBD" cannabidiol chemical name: (1'R,2'R)-5'-Methyl-4-pentyl-2'-(prop-1-en-2-yl)-1',2',3',4'-tetrahydro-[1,1'-biphenyl]-2,6-diol with no or trace delta 9 "THC" tetrahydrocannabinol molecule that is used in many beneficial therapeutic uses. Allowing producers the opportunity to sell high yield and quality superplant producing only cannabidiol (CBD) autoflowers every 45-90 days.

7 Drawing Sheets

Latin name of genus and species: *Cannabis ruderalis + Humulus lupulus.*
Variety name: 'ANEW'.

BACKGROUND OF THE DISCLOSURE

This invention relates to plant order Rosales, Family Cannabaceae and, more specifically, to an genus species referred to of *C. ruderalis*, or Binomial name *Cannabis ruderalis + Humulus lupulus*. The new Bionomial nomenclature or cultigens name was created following (ICNCP) *International Code of Nomenclature for Cultivated Plants "Cultivated Plant Code". Operating within the (ICN) International Code of Nomenclature for algae, fungi and plants.*

I discovered this new and unique strain of *Cannabaceae C. ruderalis + Humulus lupulus* as a graft chimera in a cultivated area near Jackson and Calhoun County, Mich. under the Michigan Medical Marihuana Act. The plant of this invention produces a flower of attractive commercial value that creates a plant that produces only high yield cannabidiol (CBD) and no or trace Delta-9-Tetrahydrocannabinol molecule, eliminating any psychoactive properties. This is distinct from regular *C. ruderalis, sativa,* or *indica* plants. However new strain flower quality and color characteristics are similar to those of the parent. Based on lab tests and certificates of analysis harvest in 2018 for 'ANEW' showed high levels of CBD Cannabinoids chemical name: (1'R,2'R)-5'-Methyl-4-pentyl-2'-(prop-1-en-2-yl)-1',2',3',4'-tetrahydro-[1,1'-biphenyl]-2,6-diol, minor trace amounts of Cannabinoids, CBDa, CBN, CBC, CBGa and no or trace amounts of Delta-9-THC.

This new strain of plant was asexually reproduced by top and rootstock grafting around Jackson and Calhoun County, Mich. and grafting has shown this new plant to come true in two successive generations. This propagation of the new plant by grafting under standard controlled conditions discloses the continued maintenance of the characteristics described herein which distinguish this new plant from the parent cultivar.

SUMMARY OF THE INVENTION

A new and distinct strain of *C. ruderlais*, designated 'ANEW', originated as a graft chimera in a '*C. ruderlais*' planting with a *Humulus lupulus* plant rootstock graft, creating a perennial *Cannabis rudearlis + Humulus lupulus* plant. This new and distinctive plant *C. ruderalis + Humulus lupulus* produces a flower that produces Cannabidiol CBD chemical name: (1'R,2'R)-5'-Methyl-4-pentyl-2'-(prop-1-en-2-yl)-1',2',3',4'-tetrahydro-[1,1'-biphenyl]-2,6-diol with no or trace Delta-9-THC than normal *C. ruderalis*. Flower internal quality is exceptional, being similar to the parent.

Flower skin color and appearance also are similar to '*C. ruderalis*' and *Humulus lupulus.*

DESCRIPTION OF THE DRAWINGS

This new plant of *Cannabis ruderalis* + *Humulus lupulus* 'ANEW' is illustrated by the accompanying photographic drawings and photos depicting the plant by the best possible color representation using color photography and drawings.

BOTANICAL DESCRIPTION OF THE PLANT

Figure 1:
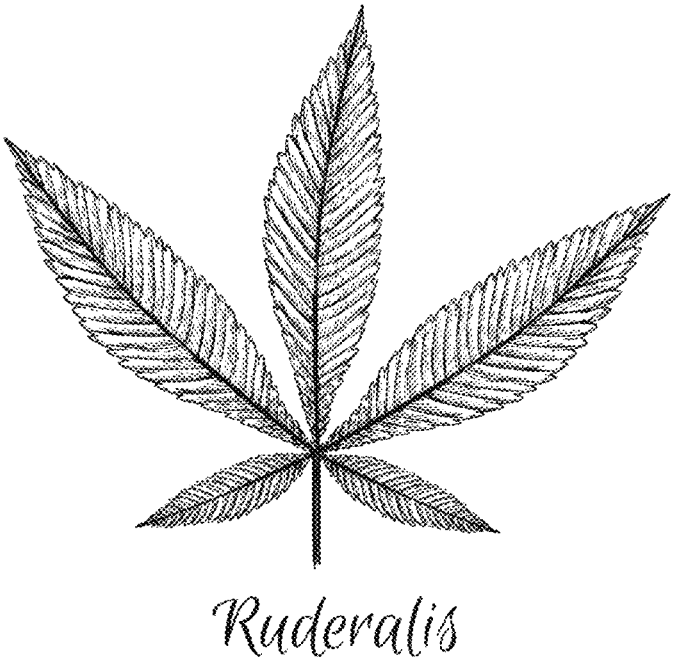
FIG. 1: Drawing showing typical leaves, leaf arrangement and leaf spacing of *C. ruderalis* plant
Figure 2:
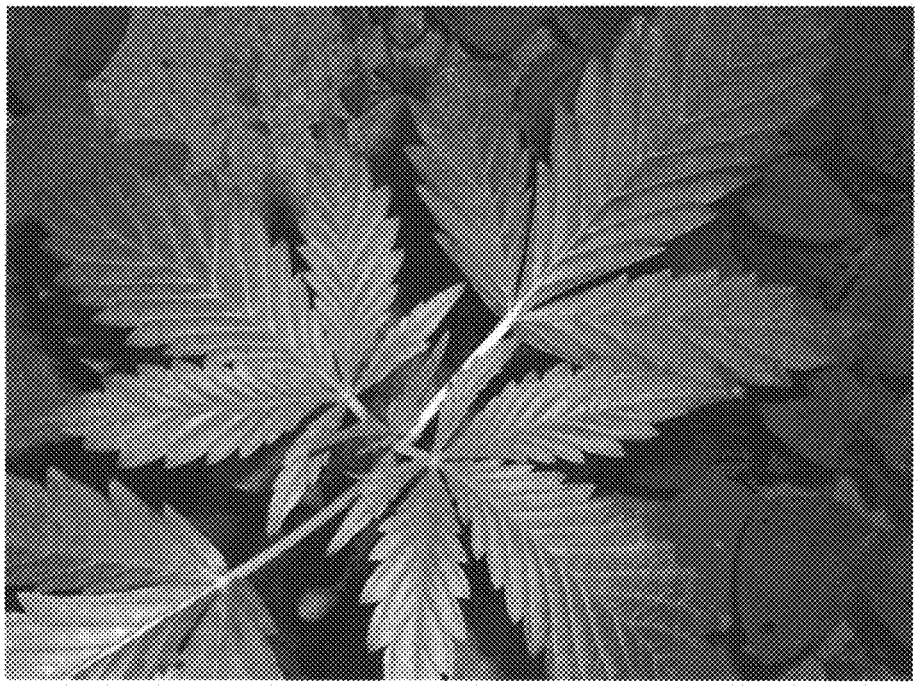
FIG. 2: Photograph showing general shape and color of season's growth, leaves, leaf arrangement and leaf spacing of *C. ruderalis*
Figure 3:
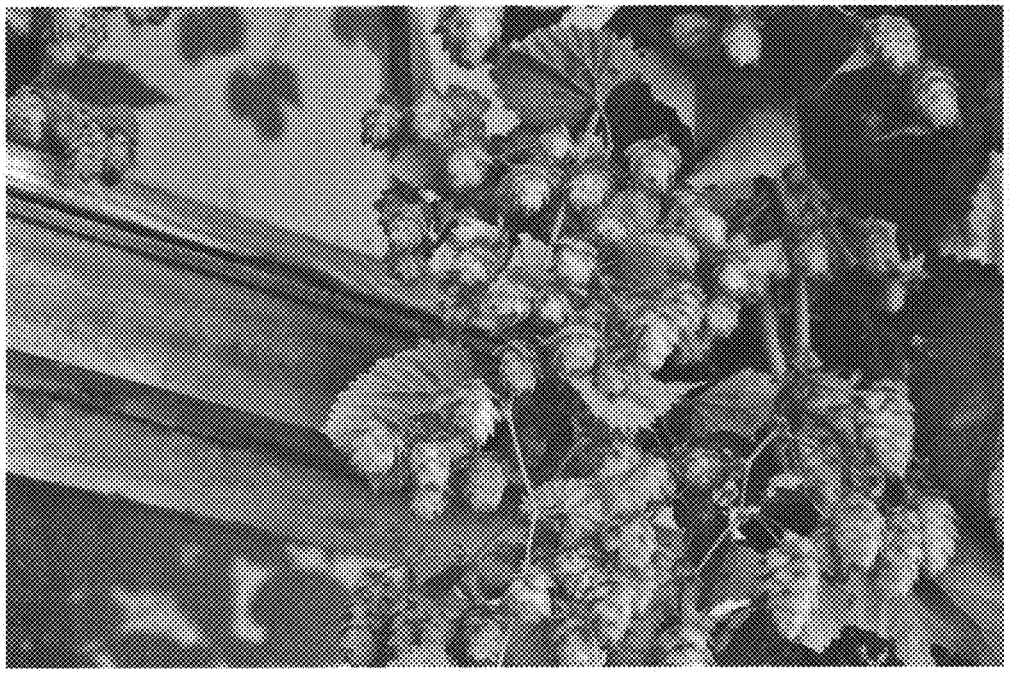
FIG. 3: Photograph showing typical leaves, leaf arrangement and leaf spacing of *Humulus lupulus*
Figure 4:
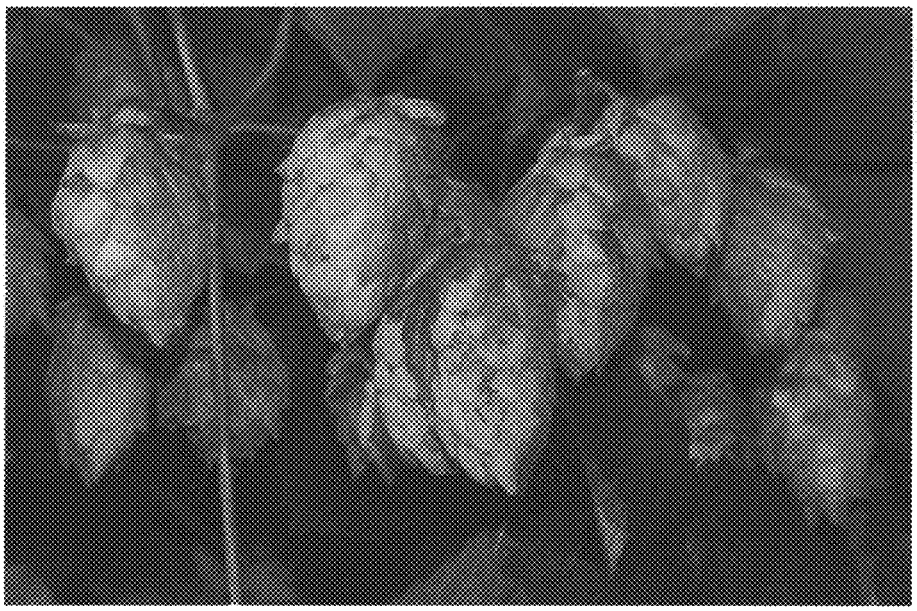
FIG. 4: Photograph showing typical leaves, branch, bark and trichomes of Humulus lupulus'
Figure 5:
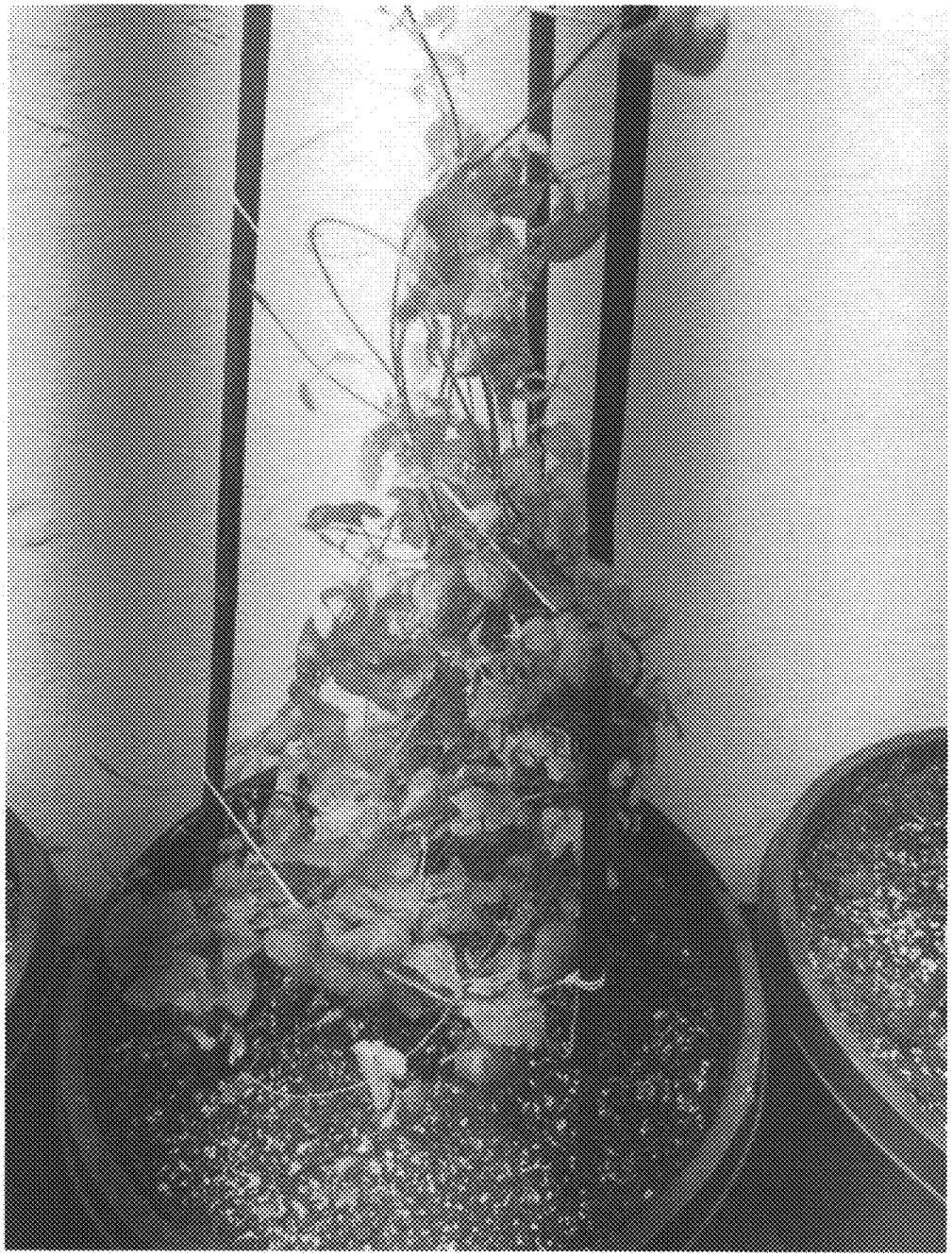
FIG. 5: Photograph showing Branch, bark, leaf and flower characteristics of 'ANEW.' Note leaves arrangement, leaf and flower characteristics, a characteristic unique to 'ANEW."
Figure 6:
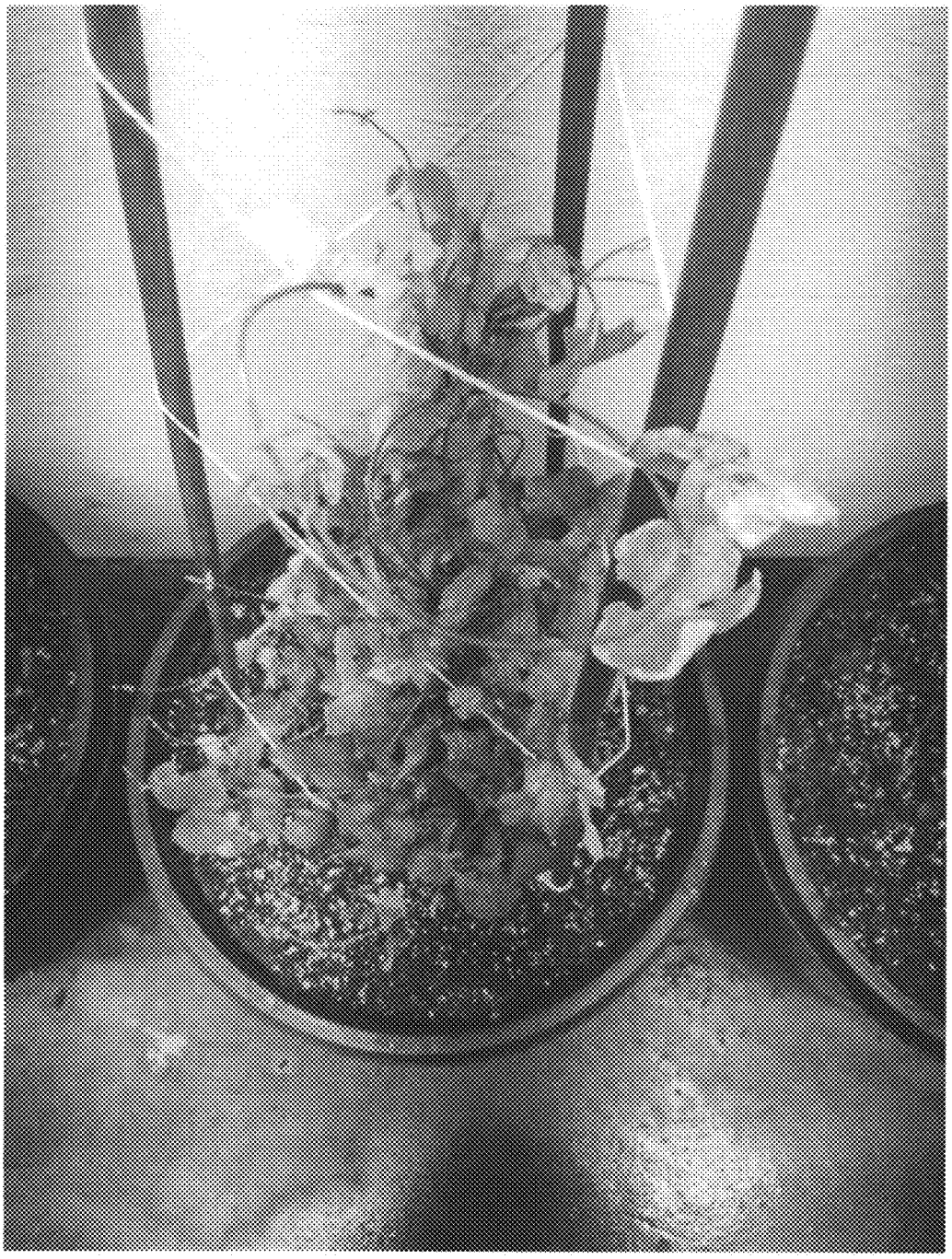
FIG. 6: Photograph showing Branch, bark, leaf and flower characteristics of 'ANEW.' Note leaves arrangement, leaf and flower characteristics, a characteristic unique to 'ANEW."
Figure 7:
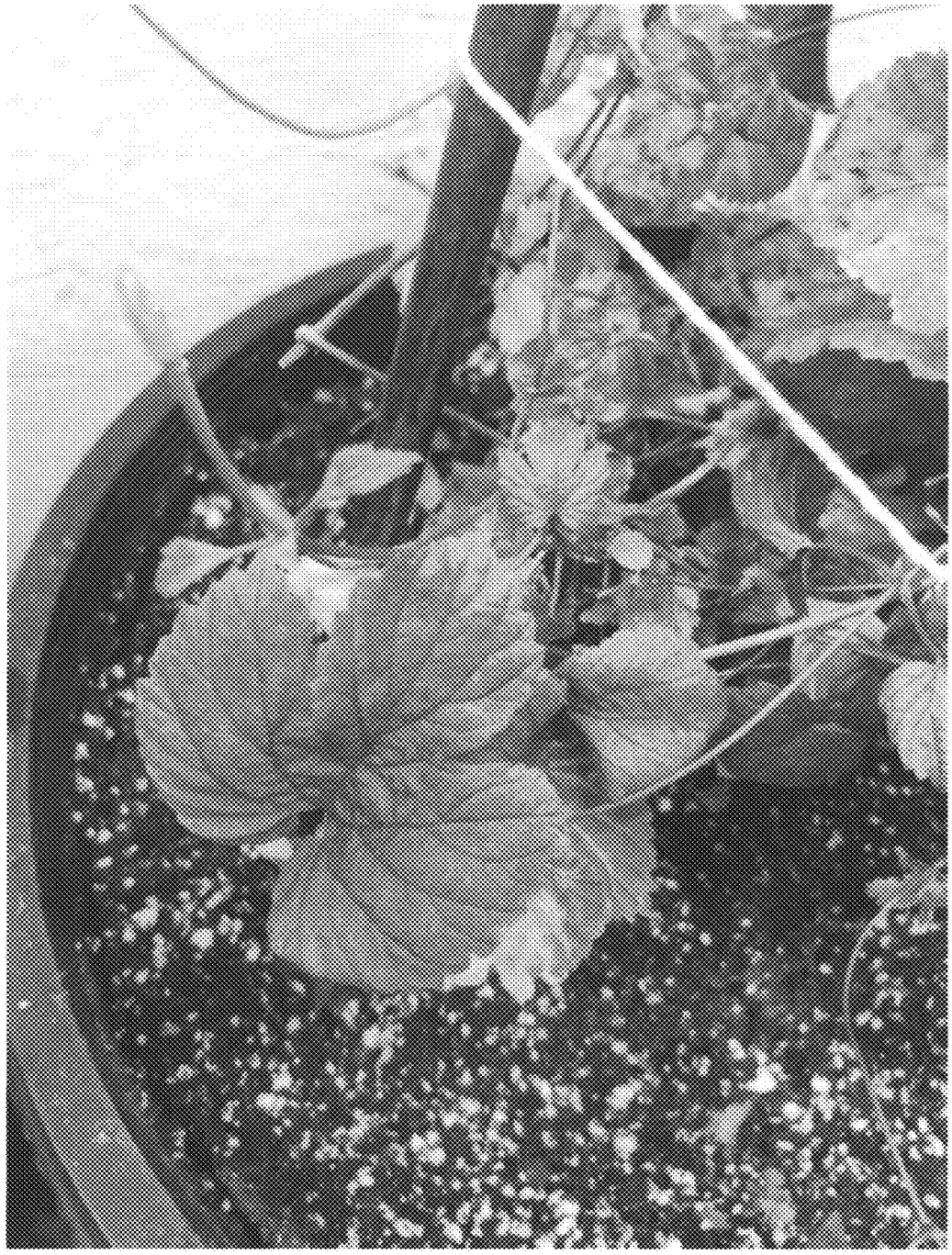
FIG. 7: Photograph showing Branch, bark, leaf and flower characteristics of 'ANEW.' Note leaves arrangement, leaf and flower characteristics, a characteristic unique to 'ANEW."

All color references below are measured against The Royal Horticultural Society Colour Chart (2015, 6th ed.). Colors are approximate as color depends on horticultural practices such as light level and fertilization rate, among others.

DETAILED BOTANICAL DESCRIPTION

This present invention relates to a new and distinct cultivar of high yield *C. ruderalis* plant, binomially known as *Cannabis ruderalis* + *Humulus lupulus* from the Cannabaceae family. The flowers produce only cannabidiol and hereinafter referred to by the cultivar name 'ANEW'. *Cannabis* comprises a genus of about 3 species of herbaceous perennials many of which, or the hybrids thereof, are suitable for cultivation in outdoors or greenhouse. *C. ruderalis* is predominantly epiphytic or ground or rockdwelling, and is native to Central and Eastern Europe and Russia. The species is typically 1 to 2.5 feet tall, has thick and sturdy stems, automatically flowers after 21-30 days of vegetation ready for harvest around 45-90 days and has 5 ranked, fleshy, oblong or elliptic leaves affixed to a short central stem (monopodial growth), which vary in size from 5 to 8 inches to over 2 feet. The leaves may be entirely green or mottled with silver grey.

A process of rootstock grafting *C. ruderalis* onto a scion of *Humulus lupulus* plant to generate a new hybridized superplant producing a high yield cannabidiol strain only 100% phytocannabinoid molecule "CBD" cannabidiol chemical name: (1'R,2'R)-5'-Methyl-4-pentyl-2'-(prop-1-en-2-yl)-1',2',3',4'-tetrahydro-[1,1'-biphenyl]-2,6-diol molecule which contains no or trace Delta-9-Tetrahydrocannabinol molecule. Creating a perennial plant generating cannabinoids for the CB1, CB2, CB3, CB4, CB5, CB6, CB7, CB8, CB9 receptors in the bodies (ECS) endocannabinoid system that have many beneficial therapeutic uses.

The following description is based on observations made during the 2016-2018 growing seasons at Jackson and Calhoun County, Mich. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average, and may vary depending on growing conditions (e.g., the amount of light). All color references are based on The Royal Horticultural Society Color Chart (2015, $6^{th}$ ed.).

Ploidy: Diploid.

Use: Brewing.

Plant shoot emergence: Generally, occurs in March of each year, but varies by year.

Flowering time: Autoflowers every 45-90 days.

Harvest date: (During early May through early October of the 2016 to 2018 growing seasons at Michigan.).

Crop yield: 1600 to 2000 pounds per acre.

Disease susceptibility: Susceptible to both powdery mildew (e.g., *Podosphaera macularis* or *Golovinomyces cichoracearum*) and downy mildew (e.g., *Pseudoperonospora cannabina*).

Aroma: A pleasant floral fruity aroma with complex savory undertones of herbal tea and eucalyptus.

Plant height: 5-10 ft.

Plant diameter: 2-3 ft.

Plant habitat: Indoor or outdoor cultivated areas.

Plant zone: Annual in Zone 5B (current zone), with USDA Hardiness zones of 8-11.

Fruit cone storage life: 1 year when cryogenically frozen.

Shipping quality: Can be packed and shipped in cool dry opaque, preferably vacuum-sealed containers. Considered "Fragile" when shipping or handling.

Analytical characteristics, as determined by gas chromatography:

- *Alpha acid* (*as % of cone weight*).—14.2% to 15.5%.
- *Beta acid* (*as % of cone weight*).—4.5% to 5.4%.
- *Cohumulone* (*as % of alpha acids*).—24.6% to 29.4%.
- *Total oil.*—1.0-2.0 ml/100 g.
- *Humulene.*—0.88-0.91% of total oils.
- *Caryophyllene.*—11.07-16.98% of total oils.
- *Myrcene.*—47.88-64.95% of total oils.
- *Farnesene.*—0.03-0.06% of total oils.
- *Cannabidiol* (*CBD*).—9.414-16.18% of total oils.
- *Tetrahydrocannabinol* (*THC*).—Minimal to none.

Bine:

- *Color.*—144B.
- *Stripe present.*—Yes.
- *Stripe color.*—60A.
- *Stipule direction.*—Up-forked.
- *Stipule color.*—144D.
- *Stipule number.*—Two per bine/branch at base of connection to stem.
- *Bine internode length.*—150 to 250 mm.
- *Bine diameter.*—8.16 mm at nine feet; 5.33 mm at terminal end of eighteen feet.
- *Bine anthocyanin coloration.*—Very weak to absent.

Laterals:

*Lateral length.*—50 to 150 cm average.

*Lateral diameter.*—3 to 5 mm average diameter at base and 0.5 to 1 mm at terminus.

*Lateral color.*—144B.

*Lateral stipule color.*—144D.

Leaf:

*Arrangement.*—Opposite.

*Shape.*—Palmately Lobed to Cordate.

*Apex shape.*—Acuminate.

*Base shape.*—Cordate.

*Average length of mature leaf.*—13.37 cm.

*Average width of mature leaf.*—18 cm.

*Surface texture of leaf upper surface.*—Smooth.

*Surface texture of leaf lower surface.*—Smooth.

*Upper surface leaf blistering.*—None.

*Color of mature leaf upper surface.*—147A.

*Color of mature leaf lower surface.*—147B.

*Color of immature leaf upper surface.*—147A.

*Color of immature leaf lower surjace.*—147B.

*Number of lobes.*—1-5.

*Number of lobes that are predominant per plant.*—1-3.

*Margin.*—Serrate.

*Serrations per inch.*—4.5.

*Average petiole length (mature).*—8.87 cm.

*Average petiole diameter.*—2 to 4 mm at base.

*Petiole color at base.*—144B, 59A.

*Petiole texture.*—Smooth with a central groove atop and slightly downy.

*Venation.*—Palmate.

*Vein color.*—145C.

Cone:

*Cone shape.*—Ovoid.

*Avg. length.*—3.365 cm.

*Avg. diameter.*—1.64 cm.

*Avg. cone weight.*—0.77 mg.

*Bract shape.*—Ovate.

*Bract length.*—7 to 11 mm average.

*Bract width.*—5 to 10 mm average.

*Bract tip color.*—145C.

*Bract base color.*—149D.

*Bract inner surface color.*—145C.

*Bract outer surface color.*—149D.

*Bract number.*—10-50+ bracts per cone, depending on size and quantity of flowers.

*Bracteole color.*—149D.

*Bract tip shape.*—Cuspidate.

*Bract tip position.*—Moderately to tightly appressed.

*Bracteole shape.*—Ovate.

*Bracteole size.*—⅛"-3⁄16".

*Lupulin glands.*—Moderate to High number of lupulin glands on average per cone.

*Lupulin gland shape.*—Pedunculated oblong polyps.

*Lupulin gland fragrance.*—Floral fruity aroma with a hint of herbal tea and eucalyptus.

*Lupulin glands.*—1⁄64"-1⁄32" and consist of two parts, a waxy, bulbous head and a stem, which comprises most of the gland, The color starts as clear, and evolves to milky white, then amber when mature.

*Pedicels.*—⅛"-½" long and have same coloring as the stem.

*Female flower.*—Female photoperiod, axillary flowers are present in a quantity of 10-30 per raceme on ½"-4" long racemes. The imperfect flowers are tightly clustered at maturity.

*Reproductive organs.*—Male flowers are loose and axillary. Individual organs are pedicellate with 5 light-green tepals and 5 stamens opposite. Stamens are flaccid. Female flowers are congested and axillary; almost sessile. Unilocular ovaries are squat with two longer filiform branches covered with small papillae to received pollen.

The invention claimed is:

1. A new and distinct strain of *Cannabis ruderalis*+ *Humulus lupulus* plant named 'ANEW' substantially as shown and described herein.

* * * * *